United States Patent [19]
Bertelli

[11] 3,978,070
[45] Aug. 31, 1976

[54] BIS-2,6-[N-(α-BENZOYLTHIOPROPIONYL)GLYCYLOXYMETHYL]PYRIDINE

[75] Inventor: Aldo Bertelli, Milan, Italy

[73] Assignee: Rorer Italiana S.p.A., Milan, Italy

[22] Filed: Sept. 9, 1975

[21] Appl. No.: 611,693

[30] Foreign Application Priority Data
Sept. 19, 1974 France .............................. 74.31623

[52] U.S. Cl. ........................... 260/294.8 G; 424/263
[51] Int. Cl.² ..................................... C07D 213/56
[58] Field of Search ............... 260/294.8 G; 424/263

[56] References Cited
UNITED STATES PATENTS
3,321,484  5/1967  Krimmel ...................... 260/295.5 R
3,432,510  3/1969  Krimmel ...................... 260/295.5 R Primary Examiner—Alan L. Rotman
Attorney, Agent, or Firm—Young & Thompson

[57] ABSTRACT

This invention relates to 2,6-bis-[N-(α-benzoylthiopropionyl)glycyloxymethyl]pyridine having the formula:

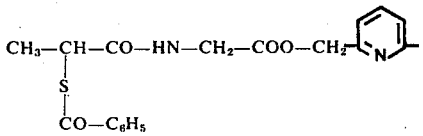

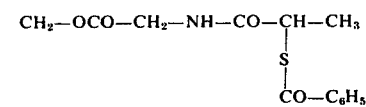

This compound possesses a protecting activity, particularly at the level of the liver, against lesions induced by toxic or infectious agents and, generally, against agents which induce hepatic and circulatory disorders and also against atherosclerotic or inflammatory lesions.

1 Claim, No Drawings

BIS-2,6-[N-(<-BENZOYLTHIOPROPIONYL)-GLYCYLOXYMETHYL]PYRIDINE

This invention relates to a new pyridine derivative which exhibits particularly a protecting activity, especially at the level of the liver, against lesions due to toxic or infectious agents and, generally, against agents which produce liver and circulatory disorders and also against atherosclerotic or inflammatory lesions.

The compound according to the present invention has the formula:

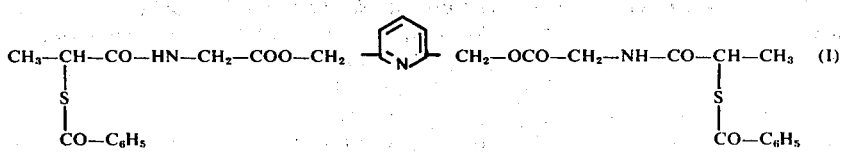

The invention encompasses also the acid addition salts of compound (I) with pharmaceutically acceptable inorganic acids (such as the hydrochloride, the sulfate, etc.) or organic acids (such as the fumarate, the citrate, the pamoate, etc.).

The preparation of compound (I) may be effected by reacting a N-(α-benzoyl-thiopropionyl)-glycine halide (II) with 2,6-dihydroxymethyl-pyridine (III).

Compound (III) is a known compound, and compound (II) may be prepared according to well known conventional methods.

The following non limiting example is given to illustrate the preparation of the compound of this invention.

EXAMPLE a. Preparation of N-(α-benzoylthiopropionyl)-glycine chloride

Thionyl chloride (10 g) is added to N-(α-benzoylthiopropionyl)-glycine (5.4 g) suspended in benzene (25 ml), with stirring. The reaction mixture is maintained at room temperature until all the solid has dissolved. The resulting yellow solution is evaporated in vacuo, taken up into benzene and again evaporated until all the remaining thionyl chloride has been removed. The residual oil is dissolved in 15 ml anhydrous chloroform.

b. Preparation of bis-2,6-[N-(α-benzoylthiopropionyl)-glycyloxy-methyl]-pyridine To the solution obtained as described under (a) above, maintained at 10°C, is added 2,6-dihydroxymethylpyridine (1.3 g) dissolved in anhydrous pyridine (10 ml), with stirring and under a nitrogen atmosphere. The addition is conducted without exceeding a temperature of 0°C. On completion of the addition, the reaction mixture is left aside at room temperature during 48 hours, after which the solvent is evaporated under a nitrogen atmosphere. The residue is then treated with a saturated sodium carbonate solution and extracted repeatedly with chloroform. The extracts are dried over $Na_2SO_4$ and are then concentrated to 25 ml. This solution is submitted to column chromatography (silica gel, 150 g), using chloroform as eluent. The main fraction, consisting of the desired 2,6-dihydroxy-methyl-pyridine diester still containing some impurities is again submitted to a short column chromatography over silica gel and is then eluted with chloroform. The product, which melts at 86°C, exhibits a spectroscopic analysis (I.R. and N.M.R.) and an elementary analysis consistent with the structure of aforesaid formula (I).

The compound according to this invention possesses an anti-toxic, liver-protecting and anti-atherosclerotic activity which makes it particularly valuable for therapeutic purposes.

The results of toxicological and pharmacological investigations carried out with the compound of this invention are given below for illustrative purposes.

1. Toxicological Investigation

The product is found to have little toxicity. The tests carried out have shown the $LD_{50}$ of the compound to be 1.45 g and 1.75 g, by the oral route, in rats and mice, respectively. In guinea-pigs, oral $LD_{50}$ is 1.05 g.

The intraperitoneal $DL_{50}$ in mice is 625 mg/kg.

The chronic toxicity of the compound is also most favourable. Daily administration in rats of 200 mg/kg of the compound, during 2 months, by the oral route, is well tolerated.

No change was found on examination of the weight of the test animals, of the blood picture, of azotemia and of the urinary excretion.

Also, no change was noted on histological examination at the level of the main organs.

2. Pharmacological Investigation a. Anti-toxic protecting action against intoxication induced by heavy metals The protection developed by the compound of this invention against experimental intoxications induced by administration of mercury chloride or sodium ethyl-mercury-thiosalicylate in mice was evaluated.

Pre-administration of 200 mg/kg of the compound of this invention, by the intraperitoneal route, provides substantially 100% protection in the animals given an intraperitoneal administration of 20 mg/kg mercury chloride or 100 mg/kg sodium ethyl-mercury-thiosalicylate.

The compound was found to have the same protecting effect at a dosage of 250 mg/kg against death induced in mice by intraperitoneal administration of 50 mg/kg copper sulfate or 200 mg/kg copper phosphate.

b. Protecting action against carbon tetrachloride-induced experimental intoxication.

Administration of carbon tetrachloride ($CCl_4$) in rats induces an early modification of the metabolism of the liver which is usually evidenced by a substantial lipidic infiltration of this organ.

In the experiments carried out, intraperitoneal or oral administration of the compound of this invention, at a dosage of 100 or 200 mg/kg prevents lipidic infiltration at the level of the liver induced by oral administration of 10 cc/kg of a $CCl_4$ solution at 10% concentration in olive oil.

c. Protecting action against ethionine-induced experimental intoxication

Lipidic hepatic infiltration in rats, induced by intraperitoneal administration of 1 g/kg ethionine divided in three doses administered in a single day is inhibited by oral administration of 200 mg/kg of the compound of this invention 8 days prior to the challenge administration.

d. Protecting action against pressurized-oxygen-induced intoxication

At an oral dosage of 300 mg/kg, the compound of this invention prevents the onset of a convulsive condition and the death of mice enclosed in a pressurized chamber, under an oxygen pressure of 4 atmospheres.

e. Protecting action against β-aminopropionitrile-induced vascular lesions

Angiolathyrism induced in mice by a daily dosage regimen of 0.4% β-aminopropionitrile during 30 days is inhibited by the administration, during the same period of time, of 4% of the compound of this invention. The vascular lesions are much less apparent, even on microscopic examination, in the animals treated with the compound of this invention.

f. Anti-atherosclerotic action

The simultaneous administration of 20 mg/kg/day of the compound of this invention in rabbits fed a hypercholesterolemia-inducing diet (1% cholesterol in the food) during 10 weeks prevents hypercholesterolemia and the formation of atherosclerotic lesions at the level of the aorta and of the arteries.

g. Anti-bradykinine action

The phlogogenic action of bradykinine is reduced by administration of the compound of this invention. Indeed, 200–400 mg/kg of the compound, on oral administration, prevent the edema of the paw of rats induced by injection of 0.5 ml of a bradykinine solution.

h. Action against blood-platelet aggregation

ADP (adenosine diphosphate) -induced blood-platelet aggregation is inhibited both in vivo and in vitro by the presence of the compound of this invention.

The compounds of the present invention are indicated for future study in human therapy in the areas of atherosclerosis and as anti-inflammatory agents against certain lesions, on the basis of data obtained in standard tests on mice, rats, and guinea pigs.

Having Now Described My Invention What I Claim as New and Desire to Secure by Letters Patent is:

1. A compound selected from the group consisting of bis-2,6-[N-(α-benzoylthiopropionyl)glycyloxymethyl]-pyridine having the formula:

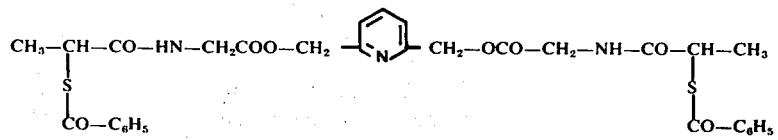

and its pharmaceutically acceptable acid addition salts.

* * * * *